(12) United States Patent
Han et al.

(10) Patent No.: US 11,872,062 B2
(45) Date of Patent: Jan. 16, 2024

(54) MEDICAL DEVICE AND METHOD FOR CONTROLLING MEDICAL DEVICE, AND STORAGE MEDIUM

(71) Applicant: SHENZHEN MINDRAY BIO-MEDICAL ELECTRONICS CO., LTD., Shenzhen (CN)

(72) Inventors: Jiang Han, Shenzhen (CN); Xianghui Wang, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 191 days.

(21) Appl. No.: 17/463,530

(22) Filed: Aug. 31, 2021

(65) Prior Publication Data

US 2022/0061777 A1    Mar. 3, 2022

(30) Foreign Application Priority Data

Sep. 1, 2020  (CN) ........................ 202010906230.X

(51) Int. Cl.
*G06F 1/00* (2006.01)
*A61B 5/00* (2006.01)
(Continued)

(52) U.S. Cl.
CPC ............ *A61B 5/7475* (2013.01); *A61B 5/002* (2013.01); *A61B 5/02055* (2013.01); *A61B 5/30* (2021.01);
(Continued)

(58) Field of Classification Search
CPC ... A61B 5/7475; A61B 5/002; A61B 5/02055; A61B 5/30; A61B 5/742; A61B 5/746;
(Continued)

(56) References Cited

U.S. PATENT DOCUMENTS

2002/0065509 A1* 5/2002 Lebel ........................ G06F 8/65
604/892.1
2008/0243210 A1* 10/2008 Doron ................ A61N 1/37217
607/60

(Continued)

FOREIGN PATENT DOCUMENTS

EP        2482167 A1    8/2012

OTHER PUBLICATIONS

Extended European Search Report issued in related European Application No. 21194440.0, dated Jan. 26, 2022, 13 pages.

*Primary Examiner* — Volvick Derose
(74) *Attorney, Agent, or Firm* — BAYES PLLC

(57) ABSTRACT

The disclosure provides a medical device and a control method therefor, and a storage medium. The medical device includes a main control circuit, a power module, and functional modules for implementing medical functions of the medical device. The functional modules are powered by the power module and controlled by the main control circuit. The main control circuit is used to determine an idle module in an idle state among the functional modules and set the idle module to be in a low-power state. On the basis of the medical device and the control method therefor and the storage medium according to the embodiments of the disclosure, the overall power consumption of the medical device can be reduced, and the battery life of the medical device is improved.

20 Claims, 8 Drawing Sheets

(51) Int. Cl.
*G16H 40/40* (2018.01)
*A61B 5/30* (2021.01)
*A61B 5/0205* (2006.01)
*G06F 1/3206* (2019.01)
*G06F 1/3212* (2019.01)

(52) U.S. Cl.
CPC .............. *A61B 5/742* (2013.01); *A61B 5/746* (2013.01); *G06F 1/3206* (2013.01); *G06F 1/3212* (2013.01); *G16H 40/40* (2018.01); *A61B 2560/0209* (2013.01); *Y02D 10/00* (2018.01)

(58) Field of Classification Search
CPC . A61B 2560/0209; A61B 5/0002; A61B 5/01; A61B 5/021; A61B 5/0215; A61B 5/0816; A61B 5/14542; A61B 5/318; G06F 1/3206; G06F 1/3212; G06F 1/26; G06F 1/3228; G06F 1/3287; G16H 40/40; G16H 10/40; G16H 10/60; G16H 40/20; G16H 40/63; Y02D 10/00; Y02D 30/50; H02J 7/0063; H02J 7/007
USPC ........................................................ 713/323
See application file for complete search history.

(56) References Cited

U.S. PATENT DOCUMENTS

| | | | |
|---|---|---|---|
| 2009/0248115 A1* | 10/2009 | Corndorf | A61N 1/37252 607/60 |
| 2011/0093729 A1* | 4/2011 | Mucignat | G06F 1/3203 713/323 |
| 2012/0157755 A1* | 6/2012 | D'Ambrosio | A61M 60/178 600/16 |
| 2015/0375003 A1* | 12/2015 | Meskens | A61N 1/37223 607/57 |
| 2017/0003356 A1* | 1/2017 | Kaib | A61N 1/3708 |
| 2018/0221662 A1* | 8/2018 | Devcic | H02J 7/0063 |
| 2018/0368066 A1* | 12/2018 | Howell | G16H 40/40 |
| 2020/0297286 A1* | 9/2020 | Costa | A61B 5/7292 |
| 2022/0061777 A1* | 3/2022 | Han | A61B 5/30 |
| 2022/0193432 A1* | 6/2022 | Apperson | A61N 1/32 |
| 2023/0014216 A1* | 1/2023 | Pan | G01R 31/3646 |
| 2023/0022909 A1* | 1/2023 | Chen | H02J 7/0044 |
| 2023/0025409 A1* | 1/2023 | Freeman | A61N 1/39044 |
| 2023/0120653 A1* | 4/2023 | Zerhusen | G16H 40/63 700/279 |

\* cited by examiner

MEDICAL DEVICE AND METHOD FOR CONTROLLING MEDICAL DEVICE, AND STORAGE MEDIUM

CROSS-REFERENCE OF RELATED APPLICATION

The application claims the benefit of priority to Chinese Application No. 202010906230.X, filed Sep. 1, 2020, the content of which is incorporated by reference in its entirety.

TECHNICAL FIELD

The disclosure relates to the technical field of medical devices, and more particularly to a medical device and a control method therefor, and a storage medium.

BACKGROUND

Existing medical devices, such as a vital sign monitor, can be usually powered by a battery. When these medical devices are powered by a battery, their internal functional modules are still in a working state even if they are not operated by a user, resulting in high power consumption of the whole medical device and short battery life.

In addition, when these medical devices access to alternating current (AC) mains, even if they are idle, their internal functional modules are still in a working state, resulting in high power consumption, and the power module load will continue to be high. In order to ensure that the other loads in the device have sufficient drive current and to maintain a constant temperature rise in the device, the battery charging current in the device is relatively small, such that the battery charging speed is slow.

In addition, the current charging speed of the existing medical devices includes only two levels, including one level when starting up and one level when shutting down. The charging speed is slow when starting up, which is mainly caused by the excessive temperature rise in the device during charging.

In general, when the existing medical devices are in use, the power consumption is large, the battery life is short, and the battery charging speed is slow.

SUMMARY

In order to solve at least one of the problems mentioned above, the disclosure provides a medical device and a control method therefor, which can reduce the power consumption of the medical device and improve the battery life of the medical device. The solution proposed in the disclosure will be briefly described below, and more details will be subsequently described in the particular embodiments in conjunction with the accompanying drawings.

In one aspect, the disclosure provides a medical device, which is switched between at least two working modes, with at least one preset workflow being included in each of the working modes, the preset workflow including at least one medical function, and the medical functions included in the two working modes being at least partially the same, the medical device including a main control circuit, a power module, and functional modules for implementing medical functions of the medical device, with the functional modules being powered by the power module and controlled by the main control circuit, where the main control circuit is used to determine an idle module in an idle state among the functional modules and set the idle module to be in a low-power state.

In another aspect, the disclosure provides a medical device, including a main control circuit, a power module, and functional modules for implementing medical functions of the medical device, with the functional modules being powered by the power module and controlled by the main control circuit, where the main control circuit is used to determine an idle module in an idle state among the functional modules and set the idle module to be in a low-power state.

In still another aspect, the disclosure provides a medical device, which is switched between at least two working modes, with at least one preset workflow being included in each of the working modes, the preset workflow including at least one medical function, and the medical functions included in the two working modes being at least partially the same. The medical device includes a main control circuit, a rechargeable power module, and functional modules for implementing medical functions of the medical device, with the functional modules being powered by the rechargeable power module and controlled by the main control circuit. The main control circuit is used to determine the power consumption of each of the functional modules when the rechargeable power module is charged, and adjust the charging power of the rechargeable power module when the total power consumption of all the functional modules changes.

In yet another aspect, the disclosure provides a medical device, including a main control circuit, a rechargeable power module, and functional modules for implementing medical functions of the medical device, with the functional modules being powered by the rechargeable power module and controlled by the main control circuit. The main control circuit is used to determine the power consumption of each of the functional modules when the rechargeable power module is charged, and adjust the charging power of the rechargeable power module when the total power consumption of all the functional modules changes.

In still another aspect, the disclosure provides a control method for a medical device, the method being performed by a main control circuit of the medical device, the medical device being switched between at least two working modes, with at least one preset workflow being included in each of the working modes, the preset workflow including at least one medical function, and the medical functions included in the two working modes being at least partially the same. The method includes determining an idle module in an idle state among functional modules, except the main control circuit and a power module for power supply, in the medical device; and setting the determined idle module to be in a low-power state.

In yet another aspect, the disclosure provides a control method for a medical device, the method being performed by means of the main control circuit of the medical device, the method including: determining an idle module in an idle state among functional modules, except the main control circuit and a power module for power supply, in the medical device; and setting the determined idle module to be in a low-power state.

In still another aspect, the disclosure provides a control method for a medical device, the method being performed by a main control circuit of the medical device, the medical device being switched between at least two working modes, with at least one preset workflow being included in each of the working modes, the preset workflow including at least one medical function, and the medical functions included in the two working modes being at least partially the same. The method includes: determining, when the rechargeable power module of the medical device is charged, the power consumption of the functional modules, except the main control circuit and the rechargeable power module, in the medical device; and adjusting the charging power of the rechargeable power module when the total power consumption of all the functional modules changes.

In yet another aspect, the disclosure provides a control method for a medical device, the method being performed by means of the main control circuit of the medical device, the method including: determining, when the rechargeable power module of the medical device is charged, the power consumption of the functional modules, except the main control circuit and the rechargeable power module, in the medical device; and adjusting the charging power of the rechargeable power module when the total power consumption of all the functional modules changes.

In still another aspect, the disclosure provides a storage medium, which is stored with a computer program that executes the control method for a medical device mentioned above.

On the basis of the medical device and the control method therefor and the storage medium according to the embodiments of the disclosure, an idle module in a idle state is determined in real time, and the idle module is set to be in a low-power state, thereby reducing the overall power consumption of the medical device and improving the battery life of the medical device. In addition, on the basis of the medical device and the control method therefor and the storage medium according to the embodiments of the disclosure, the power consumption of each of the functional modules is determined in real time when the rechargeable power module thereof is charged, and the charging power of the rechargeable power module thereof is adjusted when the total power consumption of all the functional modules changes, thereby improving the charging flexibility and providing the possibility to increase the charging speed.

DETAILED DESCRIPTIONS

In order to make the objectives, technical solutions, and advantages of the disclosure more obvious, example embodiments according to the disclosure will be described in detail below with reference to the accompanying drawings. Apparently, the described embodiments are merely some rather than all of the embodiments of the disclosure. It should be understood that the example embodiments described herein do not constitute any limitation to the disclosure. All other embodiments derived by those skilled in the art without creative efforts on the basis of the embodiments of the disclosure described in the disclosure shall fall within the scope of protection of the disclosure.

In the following description, a large number of specific details are given to provide a more thorough understanding of the disclosure. However, it is obvious to those skilled in the art that the disclosure can be implemented without one or more of these details. In other examples, to avoid confusion with the disclosure, some technical features known in the art are not described.

It should be understood that the disclosure can be implemented in different forms and should not be construed as being limited to the embodiments presented herein. On the contrary, these embodiments are provided to achieve thorough and complete disclosure and fully pass the scope of the disclosure to those skilled in the art.

The terms used herein are only intended to describe the specific embodiments and do not constitute a limitation to the disclosure. As used herein, the singular forms of "a", "an", and "said/the" are also intended to include plural forms, unless the context clearly indicates otherwise. It should also be appreciated that the terms "composed of" and/or "including", when used in the specification, determine the existence of described features, integers, steps, operations, elements, and/or components, but do not exclude the existence or addition of one or more other features, integers, steps, operations, elements, components, and/or groups thereof. As used herein, the term "and/or" includes any and all combinations of relevant listed items.

For a thorough understanding of the disclosure, detailed steps and detailed structures will be provided in the following description to explain the technical solutions proposed by the disclosure. The preferred embodiments of the disclosure are described in detail as follows. However, in addition to these detailed descriptions, the disclosure may further have other implementations.

Figure 1:
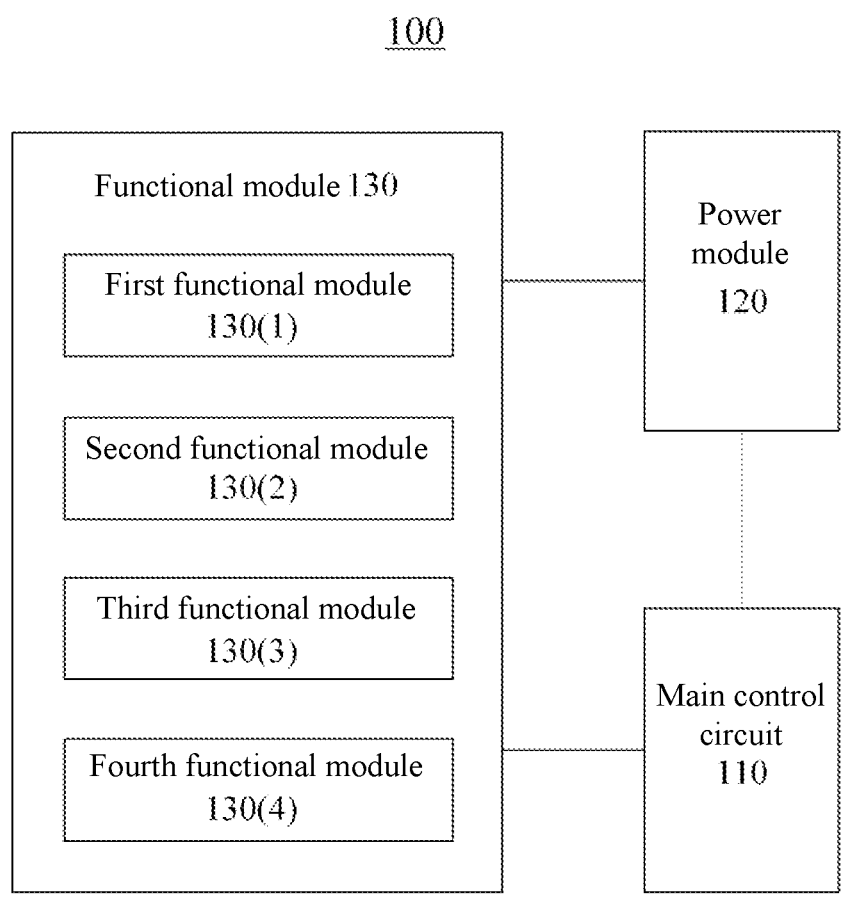
FIG. 1 shows a schematic block diagram of a medical device according to an embodiment of the disclosure.

First, a medical device according to an embodiment of the disclosure is described with reference to FIG. 1. FIG. 1 shows a schematic block diagram of a medical device 100 according to an embodiment of the disclosure. As shown in FIG. 1, the medical device 100 includes a main control circuit 110, a power module 120, and functional modules 130 for implementing medical functions of the medical device 100. The functional modules 130 are powered by the power module 120 and controlled by the main control circuit 110. The main control circuit 110 is used to determine an idle module in an idle state among the functional modules 130 and set the idle module to be in a low-power state.

In an embodiment, the medical device 100 includes a monitor or a module assembly, and further includes multiple monitors or multiple module assemblies, such as a single-parameter monitor, a multi-parameter monitor, a vital sign monitor, and a ward round monitor. The monitor or the module assembly has at least one working mode, and monitors physiological parameters of a monitored object in the working mode. It could be understood that, in one working mode, it is possible to have only one medical function, and is also possible to have multiple medical functions. In the case of multiple medical functions, there may be a requirement of sequence among the multiple medical functions. The medical device 100 may perform one or more different medical functions in different working modes. The medical functions included in the two working modes are at least partially the same, and the methods for performing the same medical function in different modes are at least partially different. A user may define physiological parameters, such as body temperature and blood pressure, that are obtained by means of parameter measurement accessories at the desired time interval or frequency, and may also define medical functions, such as urine volume, that are manually input by the user instead of the parameter measurement accessories.

In an embodiment, the medical device 100 has at least two working modes, including a continuous monitoring working mode and a discontinuous monitoring working mode. The discontinuous monitoring working mode is suitable for use in the single or multiple monitoring of a target during the evaluation on admission to hospital, the initial examination or hospitalization thereof. The continuous monitoring working mode is suitable for use in the continuous acquisition for physiological parameters of a target for a period of time and the continuous monitoring for the target. In the continuous monitoring mode in an embodiment, the medical device 100 automatically obtains physiological parameters at a certain time interval, which may be 1 millisecond, 1 second, 5 minutes, 30 minutes, 6 hours, 12 hours, etc., which is not limited here. In each working mode, the types of the obtained physiological parameters, the measurement frequency of the physiological parameters, the calculation methods for the physiological parameters, the display methods for the physiological parameters, alarm setups, and other configuration information may be different, and may be determined by the default configuration information or may be configured and modified by the user in a user-defined manner. The name of each working mode may be set by the user as desired, which is not limited here.

In this embodiment of the disclosure, the functional modules 130 may be modules for implementing medical functions of the medical device 100, such as a parameter measurement circuit (e.g., an ECG signal parameter measurement circuit, a respiration parameter measurement circuit, a body temperature parameter measurement circuit, a blood oxygen parameter measurement circuit, a non-invasive blood pressure parameter measurement circuit, and an invasive blood pressure parameter measurement circuit), a display, an alarm circuit, and an interface circuit.

In this embodiment of the disclosure, the medical device 100 includes at least one functional module 130. For the convenience of description, FIG. 1 shows that the medical device includes four functional modules, respectively shown as a first functional module 130(1), a second functional module 130(2), a third functional module 130(3) and a fourth functional module 130(4), which are collectively referred to as the functional modules 130. It should be understood that this is only exemplary, and the medical device according to the embodiment of the disclosure may include any number of functional modules.

In this embodiment of the disclosure, the main control circuit 110 may include a processor and a memory (not shown in FIG. 1), and the memory is stored with computer instructions that are executed by the processor to control the functional module 130. In this embodiment of the disclosure, the main control circuit 110 determines an idle module in an idle state among the functional modules 130. For example, in the example shown in FIG. 1, the main control circuit 110 may determine which module or modules among the first functional module 130(1), the second functional module 130(2), the third functional module 130(3) and the fourth functional module 130(4) are in the idle state.

In an embodiment of the disclosure, the idle module may be a functional module that has not received a user operation within a predetermined time interval. In this embodiment, determining the idle module by means of the main control circuit 110 may include: determining, for each functional module 130, if the functional module 130 has not received a user operation within a predetermined time interval, the functional module to be an idle module in an idle state. In this embodiment, the main control circuit 110 may determine whether the functional module 130 is an idle module by means of monitoring the user's operation on the functional module 130. For example, after each operation of the user, a timer (not shown, which may be included inside or outside the main control circuit 110) may be used to start timing. If the user does not operate the functional module 130 for a long time (e.g., exceeding the threshold of the predetermined time interval), the functional module 130 may be determined to be an idle module. In this embodiment, the idle module is determined according to the detection for the user operation, which is simple to implement.

In another embodiment of the disclosure, the idle module may be a functional module that is not in its predefined working time. In this embodiment, determining the idle module by means of the main control circuit 110 may include: determining the working time of each functional module 130 according to the preset workflow, and determining the functional module 130, which is not in the working time, as the idle module in the idle state. For example, according to the preset workflow, the working time of the first functional module 130(1) is a to b, the working time of the second functional module 130(2) is c to d, the working time of the third functional module 130(3) is e to f, and the working time of the fourth functional module 130(4) is g to h, where a, b, c, d, e, f, g and h are each a time point, and some of them may be the same time point, or they may all be different time points. In other words, the working time of each functional module 130 may be the same, or different, or partially the same. In summary, the preset working time of each functional module 130 is determined by means of the preset workflow. If one functional module 130 is in its working time, the main control circuit 110 may regard same as a non-idle module; and conversely, if one functional module 130 is not in its working time, the main control circuit 110 may regard same as an idle module. In this embodiment, the idle module is determined according to the preset workflow without continuously monitoring the functional module in real time, which is simple to implement.

In a still another embodiment of the disclosure, the idle module may be a functional module designated by a user. In this embodiment, determining the idle module by means of the main control circuit 110 may include: receiving an instruction that is input by a user for designating an idle module among the functional modules 130, and determining the idle module among the functional modules 130 according to the instruction. For example, a user may input an instruction via user interaction apparatus (not shown, such as a touch display screen of the medical device 100) internal or external to the medical device 100 to designate which module or modules among the first functional module 130(1), the second functional module 130(2), the third functional module 130(3) and the fourth functional module 130(4) are in the idle state. After receiving the instruction, the main control circuit 110 determines the idle module in the idle state among the functional modules 130 according to the user instruction. In this embodiment, the idle module is determined according to the user instruction in real time, which is implemented flexibly.

In the other embodiments of the disclosure, the idle module in the idle state among the functional modules 130 may also be determined by any other suitable methods, which will not be described by examples. For example, the distance of the user from the medical device 100 is detected by means of a sensor (e.g., an infrared sensor or a radar sensor) internal or external to the medical device 100. If the distance exceeds a certain threshold (e.g., a distance threshold) for a long time (e.g., a time threshold), some or even all of the functional modules 130 may be determined as idle modules.

In this embodiment of the disclosure, when determining the idle module in the idle state among the functional modules 130, the main control circuit 110 may set the determined idle module to be in a low-power state. In this embodiment of the disclosure, the low-power state may be a state in which the power consumption is lower than that in a working state which includes a power-on state. In other words, in this embodiment of the disclosure, the functional module 130 in the idle state is set to be in a state in which the power consumption is lower than that in the power-on state, which may generally reduce the power consumption of the medical device 100, thereby improving the battery life of the medical device 100. Obviously, the more the idle modules, the more the functional modules 130 which are set to be in the low-power state, thus the more the power consumption of the overall medical device 100 is reduced, and thus the longer the battery life of the medical device 100 is.

In this embodiment of the disclosure, the low-power state of each functional module 130 may include a sleep state and a power-off state. For example, when not in measurement, the parameter measurement circuit, the display, etc., may be set to sleep, and even directly powered off.

In this embodiment of the disclosure, when each functional module 130 is set to be in the low-power state, the main control circuit 110 may enter the low-power state. In this embodiment of the disclosure, the low-power state of the main control circuit 110 may include a sleep state. Generally, the main control circuit 110 serves as a control brain that needs to wait for an external trigger at any time, and thus the low-power state of the main control circuit 110 is generally a sleep state. In addition, in the foregoing example, if the distance of the user from the medical device 100 exceeds a certain threshold for a long time, the overall medical device 100 may also enter a low-power state.

In this embodiment of the disclosure, on the basis of the user operation, the main control circuit 110 may wake up itself and/or wake up the idle module that are set to be in the low-power state. The main control circuit 110 may also wake up the idle module, which is set to be in the low-power state, in a corresponding manner according to different determination methods for the idle module. For example, if the idle module is determined according to the monitoring user operation (as described above), after the idle module is determined to receive the user operation, the idle module may also be restored to the non-idle state; if the idle module is determined according to the preset workflow (as described above), the idle module that enters its preset working time may be restored to the non-idle state; if the idle module is determined according to the user instruction (as described above), the idle module may also be restored to the non-idle state according to the user instruction; and so on.

In a further embodiment of the disclosure, the power module 120 may include a rechargeable battery. In other words, when the medical device 100 is in use or not in use, there may be a scenario in which an external power source is used to charge the rechargeable battery therein. In this embodiment of the disclosure, when the rechargeable battery of the power module 120 of the medical device 100 is charged, the main control circuit 110 may also be used to determine whether there currently exists an idle module that is set to be in a low-power state: if the main control circuit 110 determines that there is currently no idle module that is set to be in the low-power state, the charging power of the rechargeable battery may be set to be a first threshold; and if the main control circuit 110 determines that there currently exists an idle module that is set to be in the low-power state, the charging power is increased on the basis of the first threshold.

As mentioned above, when the existing medical device accesses to the AC mains so as to charge the power module, no matter whether its internal functional module is idle, it is still in the working state, such that the power consumption is still high, and the power module load will continue to be high. In order to ensure that the other loads in the device have sufficient drive current and to maintain a constant temperature rise in the device, the battery charging current in the device is relatively small, such that the battery charging speed is slow. In the above embodiments herein, the main control circuit 110 of the medical device 100 may set the functional module in the idle state (i.e., an idle module) to be in the low-power state (with the power consumption less than that in the working state). Based on this, when the rechargeable battery of the power module 120 of the medical device 100 is charged (e.g., the medical device 100 accesses to the AC mains), the main control circuit 110 may determine whether there currently exists an idle module that is set to be in the low-power state. If it doesn't exist, it indicates that all the functional modules are currently working normally and in the working state, that is, in order to ensure a constant temperature rise in the device, there is currently no room for increasing the charging power (e.g., the charging current); therefore, the charging power of the rechargeable battery may be set as a first threshold. Conversely, if the main control circuit 110 determines that there currently exists an idle module that is set to be in the low-power state, it indicates that there currently exists the room for increasing the charging power; therefore, the charging power may be increased on the basis of the first threshold. On the basis of the increased charging power, the charging speed of the rechargeable battery of the power module 120 may be increased.

In a further embodiment of the disclosure, the main control circuit 110 may determine the charging power of the rechargeable battery according to the power consumption of the idle module that is set to be in the low-power state. In other words, when the main control circuit 110 determines that there currently exists an idle module that is set to be in the low-power state, the specific power consumption of the idle modules may be further determined to obtain the reduced power consumption of the idle modules relative to the power consumption in the working state thereof. In this way, the overall reduced power consumption of all the idle modules may be obtained, and the overall reduced power consumption may provide room for increasing the charging power of the rechargeable battery of the power module 120. Exemplarily, the increased charging power of the main control circuit 110 on the basis of the first threshold mentioned above may be equal to the sum of the reduced power consumption of each functional module, which is set to be in the low-power state, relative to the power consumption in the working state, that is, equal to the overall reduced power consumption mentioned above, which may maximize the charging power of the rechargeable battery of the power module 120 and at the same time ensure that the temperature rise in the medical device 100 is constant and controllable. Alternatively, the charging power of the main control circuit 110 on the basis of the first threshold mentioned above may also be less than the sum of reduced power consumption of each functional module, which is set to be in the low-power state, relative to the power consumption in the working state.

In a further embodiment of the disclosure, when the main control circuit 110 determines that there currently exists an idle module that is set to be in the low-power state, a suitable charging level may be further selected from the preset charging levels according to the number of the idle modules that are set to be in the low-power state, with different charging levels corresponding to different charging powers. In this embodiment, different charging levels are preset, and in different charging levels, the charging power of the rechargeable battery of the power module 120 is different. For example, five charging levels are preset, including a first charging level, a second charging level, a third charging level, a fourth charging level and a fifth charging level, which five charging levels respectively correspond to a first charging power, a second charging power, a third charging power, a fourth charging power and a fifth charging power. In this example, for example, when the number of the idle modules that are set to be in the low-power state is a first value or in a first range of value, the first charging level may be selected (i.e., the first charging power is used) for charging the rechargeable battery of the power module 120; similarly, when the number of the idle modules that are set to be in the low-power state is a second value or in a second range of value, the second charging level may be selected (i.e., the second charging power is used) for charging the rechargeable battery of the power module 120; and so on. In this embodiment, by means of presetting several charging levels and selecting, by means of the main control circuit 110, a suitable charging level according to the number of the idle modules that are set to be in the low-power state. For example, when there are a larger number of the idle modules, the rechargeable battery is charged with a large-current charging level, and when there are a smaller number of the idle modules, the rechargeable battery is charged with a small-current charging level. This may further improve the charging flexibility while increasing the charging speed of the rechargeable battery of the power module 120.

In a further embodiment of the disclosure, when the idle module is restored to the working state due to wake-up or other reasons, the main control module 110 may correspondingly reduce the charging power of the rechargeable battery of the power module 120.

In another embodiment of the disclosure, the main control circuit 110 does not adjust the charging power of the rechargeable battery of the power module 120 on the basis of whether there is an idle module, but monitors the working current of each functional module in real time and adjusts the charging power of the rechargeable battery in real time according to the working current. In this embodiment, regardless of whether the functional module enters the low-power state, the working current of each functional module is monitored in real time, and once the working current of the functional module is detected to be reduced, it indicates that there is a room for increasing the charging power of the rechargeable battery of the power module 120. In this case, the charging power of the rechargeable battery of the power module 120 may be further correspondingly increased on the basis of the overall reduction in power consumption of all the functional modules, thereby increasing the charging speed. Thereafter, the main control circuit 110 may continue to monitor the working current of each functional module in real time, and once the working current of the functional module is detected to be increased, the charging power of the rechargeable battery of the power module 120 is also correspondingly reduced. According to this embodiment, it is not only possible to increase the charging speed of the rechargeable battery of the power module 120, but also achieve the very flexible adjustment of the charging power.

In yet another embodiment of the disclosure, as described in the foregoing example, the distance of the user from the medical device 100 exceeds a certain threshold for a long time, the whole medical device 100 may enter the low-power state, and in this case, the charging power of the rechargeable battery of the power module 120 may be correspondingly increased on the basis of the reduction in power consumption of the whole device, thereby increasing the charging speed.

On the basis of the above description, the medical device according to this embodiment of the disclosure determines an idle module in a idle state in real time and set the idle module to be in a low-power state, thereby reducing the overall power consumption of the medical device and improving the battery life of the medical device. In addition, on the basis of the medical device according to this embodiment of the disclosure, the power consumption of each of the functional modules is determined in real time when the rechargeable power module thereof is charged, and the charging power of the rechargeable power module thereof is adjusted when the total power consumption of all the functional modules changes, thereby improving the charging flexibility and providing the possibility to increase the charging speed.

Figure 2:
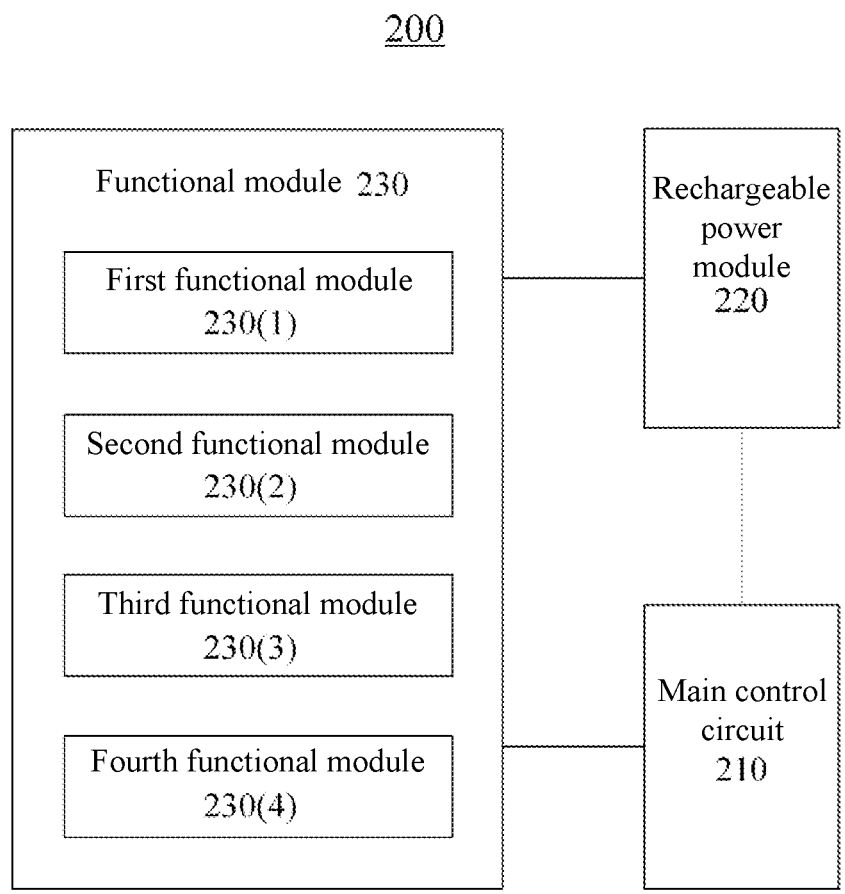
FIG. 2 shows a schematic block diagram of a medical device according to another embodiment of the disclosure.

The medical device according to another embodiment of the disclosure will be described below with reference to FIG. 2. FIG. 2 shows a schematic block diagram of a medical device 200 according to an embodiment of the disclosure. As shown in FIG. 2, the medical device 200 includes a main control circuit 210, a rechargeable power module 220, and functional modules 230 for implementing medical functions of the medical device 200. The functional modules 230 are powered by the rechargeable power module 220 and controlled by the main control circuit 210. The main control circuit 210 is used to determine the power consumption of each functional module 230 when the rechargeable power module 220 is charged, and adjust the charging power of the rechargeable power module 220 when the total power consumption of all the functional modules 230 changes.

In this embodiment of the disclosure, the functional modules 230 may be modules for implementing medical functions of the medical device 200, such as a parameter measurement circuit (e.g., an ECG signal parameter measurement circuit, a respiration parameter measurement circuit, a body temperature parameter measurement circuit, a blood oxygen parameter measurement circuit, a non-invasive blood pressure parameter measurement circuit, and an invasive blood pressure parameter measurement circuit), a display, an alarm circuit, and an interface circuit.

In this embodiment of the disclosure, the medical device 200 includes at least one functional module 230. For the convenience of description, FIG. 1 shows that the medical device includes four functional modules, respectively shown as a first functional module 230(1), a second functional module 230(2), a third functional module 230(3) and a fourth functional module 230(4), which are collectively referred to as the functional modules 230. It should be understood that this is only exemplary, and the medical device according to the embodiment of the disclosure may include any number of functional modules.

In this embodiment of the disclosure, the main control circuit 210 may include a processor and a memory (not shown in FIG. 2), and the memory is stored with computer instructions that are executed by the processor to control the functional module 230.

As mentioned above, when the existing medical device accesses to the AC mains so as to charge the power module, the battery charging current in the device is relatively small, such that the battery charging speed is slow. In this embodiment of the disclosure, when the rechargeable power module 220 is charged, the main control circuit 210 may determine the power consumption of each functional module 230, and adjust the charging power of the rechargeable power module 220 when the total power consumption of all the functional modules 230 (e.g., the first functional module 230(1), the second functional module 230(2), the third functional module 230(3) and the fourth functional module 230(4) shown in FIG. 2) changes. Adjusting the charging power of the rechargeable power module 220 by means of the main control circuit 210 may include: increasing the charging power of the rechargeable power module 220 when the total power consumption of all the functional modules 230 is reduced; and reducing the charging power of the rechargeable power module 220 when the total power consumption of all the functional modules 230 is increased. Based on this, on the basis of the medical device 200 according to this embodiment of the disclosure, the charging power of the rechargeable power module 220 may be increased when the total power consumption of all the functional modules 230 is reduced, thereby increasing the charging speed of the rechargeable power module 220. Thereafter, once the total power consumption of all the functional modules 230 is increased, the medical device 200 according to this embodiment of the disclosure may make corresponding adjustment to correspondingly reduce the charging power of the rechargeable power module 220, which may not only provide the possibility to increase the charging speed, but also achieve the flexible charging.

In this embodiment of the disclosure, when the power consumption of each functional module 230 reaches the maximum value of its own power consumption, the charging power of the rechargeable power module may be equal to a first threshold; and when the power consumption of any one of the functional modules 230 does not reach the maximum value, the charging power of the rechargeable power module 220 may be equal to a second threshold, which is equal to the first threshold plus the reduced value, relative to the maximum value, of the power consumption value of the power module that does not reach the maximum value. In other words, the overall reduced power consumption of the functional modules 230 may all be used as the room for increasing the charging power of the rechargeable power module 220, which may maximize the charging power of the rechargeable battery of the rechargeable power module 220.

In this embodiment of the disclosure, the main control circuit 210 may determine the power consumption of each functional module 230 by means of monitoring the working current of each functional module 230 in real time. Once the working current of the functional module is detected to be reduced, it indicates that there is a room for increasing the charging power of the rechargeable battery of the rechargeable power module 220.

In this embodiment of the disclosure, adjusting the charging power of the rechargeable power module 220 by means of the main control circuit 210 may include adjusting the charging current of the rechargeable power module 220. Generally, the rechargeable power module 220 may be constant, so the charging power of the rechargeable power module 220 may be adjusted by means of adjusting the charging current. Of course, in other embodiments, adjusting the charging power of the rechargeable power module 220 may be implemented by means of adjusting the charging voltage of the rechargeable power module 220, or adjusting the charging power of the rechargeable power module 220 by means of adjusting both the charging voltage and the charging current.

In a further embodiment of the disclosure, regardless of whether the rechargeable power module 220 is in a charged state, the main control circuit 210 may also be used to determine the idle module in the idle state among the functional modules 230, and set the idle module to be in the low-power state (the state in which the power consumption is lower than that in the working state, with the working state including a power-on state). This may improve the battery life of the rechargeable power module 220 when the rechargeable power module 220 is not in the charging state, and may increase the charging speed when the rechargeable power module 220 is in a charging state (because the low-power state of the functional module 230 provides room for increasing the charging power of the rechargeable power module 220).

In an embodiment of the disclosure, the idle module may be a functional module that has not received a user operation within a predetermined time interval. In this embodiment, determining the idle module by means of the main control circuit 210 may include determining, for each functional module 230, if the functional module 230 has not received a user operation within a predetermined time interval, the functional module to be an idle module in an idle state. In this embodiment, the main control circuit 210 may determine whether the functional module 230 is an idle module by means of monitoring the user's operation on the functional module 230. For example, after each operation of the user, a timer (not shown, which may be included inside or outside the main control circuit 210) may be used to start timing. If the user does not operate the functional module 230 for a long time (e.g., exceeding the threshold of the predetermined time interval), the functional module 230 may be determined to be an idle module. In this embodiment, the idle module is determined according to the detection for the user operation, which is simple to implement.

In another embodiment of the disclosure, the idle module may be a functional module that is not in its predefined working time. In this embodiment, determining the idle module by means of the main control circuit 210 may include determining the working time of each functional module 230 according to the preset workflow, and determining the functional module 230 that is not in the working time as the idle module in the idle state. For example, according to the preset workflow, the working time of the first functional module 230(1) is a to b, the working time of the second functional module 230(2) is c to d, the working time of the third functional module 230(3) is e to f, and the working time of the fourth functional module 230(4) is g to h, where a, b, c, d, e, f, g, and h are each a time point, and some of them may be the same time point, or they may all be different time points. In other words, the working time of each functional module 230 may be the same, or different, or partially the same. In summary, the preset working time of each functional module 230 is determined by means of the preset workflow. If one functional module 230 is in its working time, the main control circuit 210 may regard same as a non-idle module; and conversely, if one functional module 230 is not in its working time, the main control circuit 210 may regard same as an idle module. In this embodiment, the idle module is determined according to the preset workflow without continuously monitoring the functional module in real time, which is simple to implement.

In a still another embodiment of the disclosure, the idle module may be a functional module designated by a user. In this embodiment, determining the idle module by means of the main control circuit 210 may include: receiving an instruction that is input by a user for designating an idle module among the functional modules 230, and determining the idle module among the functional modules 230 according to the instruction. For example, a user may input an instruction via a user interaction apparatus (not shown, such as a touch display screen of the medical device 200) internal or external to the medical device 200 to designate which module or modules among the first functional module 230(1), the second functional module 230(2), the third functional module 230(3) and the fourth functional module 230(4) are in the idle state. After receiving the instruction, the main control circuit 210 determines the idle module in the idle state among the functional modules 230 according to the user instruction. In this embodiment, the idle module is determined according to the user instruction in real time, which is implemented flexibly.

In the other embodiments of the disclosure, the idle module in the idle state among the functional modules 130 may also be determined by any other suitable methods, which will not be described by examples. For example, the distance of the user from the medical device 100 is detected by means of a sensor (e.g., an infrared sensor or a radar sensor) internal or external to the medical device 100. If the distance exceeds a certain threshold (e.g., a distance threshold) for a long time (e.g., a time threshold), some or even all of the functional modules 130 may be determined as idle modules. The idle modules are set to be in the low-power state, and even the whole medical device 100 may enter the low-power state. In this case, the charging power of the rechargeable battery of the power module 120 may be correspondingly increased on the basis of the reduction in power consumption of the whole device, thereby increasing the charging speed.

In this embodiment of the disclosure, the low-power state of each functional module 230 may include a sleep state and a power-off state. For example, when not in measurement, the parameter measurement circuit, the display, etc., may be set to sleep, and even directly powered off.

In this embodiment of the disclosure, when each functional module 230 is set to be in the low-power state, the main control circuit 210 may enter the low-power state. In this embodiment of the disclosure, the low-power state of the main control circuit 210 may include a sleep state. Generally, the main control circuit 210 serves as a control brain that needs to wait for an external trigger at any time, and thus the low-power state of the main control circuit 210 is generally a sleep state.

In this embodiment of the disclosure, on the basis of the user operation, the main control circuit 210 may wake up itself and/or wake up the idle module that are set to be in the low-power state. The main control circuit 210 may also wake up the idle module, which is set to be in the low-power state, in a corresponding manner according to different determination methods for the idle module. For example, if the idle module is determined according to the monitoring user operation (as described above), after the idle module is determined to receive the user operation, the idle module may also be restored to the non-idle state; if the idle module is determined according to the preset workflow (as described above), the idle module that enters its preset working time may be restored to the non-idle state; if the idle module is determined according to the user instruction (as described above), the idle module may also be restored to the non-idle state according to the user instruction; and so on.

In this embodiment of the disclosure, similar to the medical device 100 as described above in conjunction with FIG. 1, the medical device 200 may be switched between at least two working modes, with at least one preset workflow being included in each of the working modes, the preset workflow including at least one medical function, and the medical functions included in the two working modes being at least partially the same. The user may understand the working mode described here according to the foregoing description in conjunction with FIG. 1, which will not be further described here for brevity.

Based on the above description, on the basis of the medical device according to this embodiment of the disclosure, the power consumption of each of the functional modules is determined in real time when the rechargeable power module thereof is charged, and the charging power of the rechargeable power module thereof is adjusted when the total power consumption of all the functional modules changes, thereby improving the charging flexibility and providing the possibility to increase the charging speed. In addition, the medical device according to this embodiment of the disclosure may determine the idle module in the idle state in real time and set the idle module to be in the low-power state, thereby reducing the overall power consumption of the medical device, improving the battery life of the medical device, and increasing the charging speed of the rechargeable power module when the rechargeable power module is charged.

As described with reference to FIG. 3 below, on the basis of the medical device 300 according to still another embodiment of the disclosure, the medical device 300 is exemplarily shown as a multifunctional monitor, which may be regarded as a further refinement of the structure of the medical device as described above with reference to FIG. 1 and/or FIG. 2, and the medical device may implement all the functions of the medical device as described above with reference to FIG. 1 and/or FIG. 2.

Figure 3:
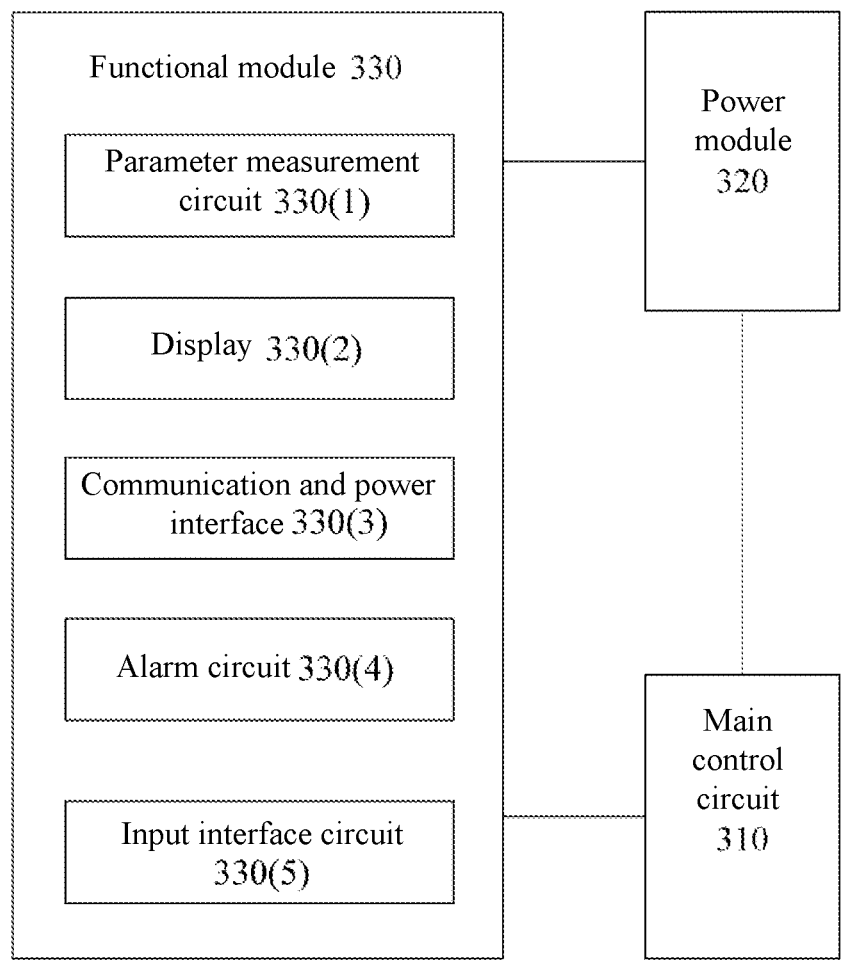
FIG. 3 shows a schematic block diagram of a medical device according to a still another embodiment of the disclosure.

As shown in FIG. 3, the medical device 300 may include a main control circuit 310, a power module 320, and functional modules 330 for implementing medical functions of the medical device 300. The functional modules 330 may further include a parameter measurement circuit 330(1), a display 330(2), a communication and power interface 330(3), an alarm circuit 330(4) and an input interface circuit 330(5).

The parameter measurement circuit 330(1) at least includes a parameter measurement circuit 330(1) corresponding to a physiological parameter, for example, an ECG signal parameter measurement circuit, a respiration parameter measurement circuit, a body temperature parameter measurement circuit, a blood oxygen parameter measurement circuit, a non-invasive blood pressure parameter measurement circuit, an invasive blood pressure parameter measurement circuit, etc., each parameter measurement circuit 330(1) being respectively connected to an externally inserted sensor accessory via a corresponding sensor interface. For example, the sensor accessory may include detection accessories corresponding to measurement of physiological parameters such as ECG, respiration, blood oxygen, blood pressure and body temperature. Specifically, the parameter measurement circuit 330(1) obtains physiological sampling signals of the relevant patient from the sensor accessory, and obtains physiological data after processing for alarming and displaying.

The main control circuit 310 may include at least one processor and at least one memory. Of course, the main control circuit 310 may also include a power management module. The power management module is used to control the power on and off of the whole device, the power-on sequence of each power domain inside a board card, battery charging and discharging, etc. The main control circuit 310 may be used to control the data interaction between the parameter measurement circuit 330(1) and the communication and power interface 330(3), control the transmission of signals, and transfer the physiological data to the display 330(2) for displaying, and may also receive user control instructions which are input from a touch screen or a physical input interface circuit 330(5) such as a keyboard and keys, and of course, may also output control signals on how to collect the physiological parameters. The alarm circuit 330(4) may be an audible and visual alarm circuit. The main control circuit 310 completes the calculation of physiological parameters, and may send the calculation results and waveforms of the parameters to the main unit via the communication and power interface 330(3). The communication and power interface 330(3) may also be one or a combination of a wireless data transmission interface and a wired data transmission interface. The main unit may be a main unit of the monitor, an electrocardiograph, an ultrasonic diagnosis instrument, or any computer device such as a computer, and may be installed with matching software to form a monitoring device. The main unit may also be a communication device such as a mobile phone, and the medical device 300 may send, via a Bluetooth interface, data to a mobile phone that supports Bluetooth communication to implement remote transmission of the data.

In this embodiment of the disclosure, the main control circuit 310 may determine, in real time, the idle module in the idle state among the functional modules 330 including the parameter measurement circuit 330(1), the display 330 (2), the communication and power interface 330(3), the alarm circuit 330(4) and the input interface circuit 330(5), and set the idle module to be in the low-power state, thereby reducing the overall power consumption of the medical device and improving the battery life of the medical device. In addition, the main control circuit 310 may determine the power consumption of each functional module 330 in real time when the power module 320 thereof is charged, and adjust the charging power of the power module 320 thereof when the total power consumption of all the functional modules 330 changes, thereby improving the charging flexibility and providing the possibility to increase the charging speed.

In this embodiment of the disclosure, similar to the medical device 100 as described above in conjunction with FIG. 1, the medical device 300 may be switched between at least two working modes, with at least one preset workflow being included in each of the working modes, the preset workflow including at least one medical function, and the medical functions included in the two working modes being at least partially the same. The user may understand the working mode described here according to the foregoing description in conjunction with FIG. 1, which will not be further described here for brevity.

The medical device according to this embodiment of the disclosure is exemplarily shown as above. A control method for a medical device provided according to another aspect of the disclosure will be shown below in conjunction with FIGS. 4 to 8. The following control methods may all be implemented by means of a main control circuit of the medical device. The medical devices according to this embodiment of the disclosure as described above may all implement the following control methods. Since some technical details have been described in detail above, the description of some technical details is omitted below for brevity, and those skilled in the art could have understood the technical details of the following methods with reference to the foregoing description.

Figure 4:
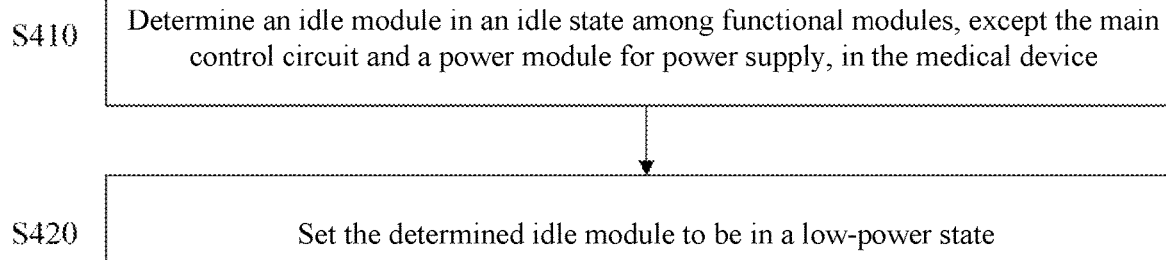
FIG. 4 shows a schematic flow diagram of a control method for a medical device according to an embodiment of the disclosure.

FIG. 4 shows a schematic flow diagram of a control method 400 for a medical device according to an embodiment of the disclosure. As shown in FIG. 4, the control method 400 for the medical device may include the following steps.

At step S410, an idle module in an idle state among functional modules, except the main control circuit and a power module for power supply, in the medical device is determined.

At step S420, the determined idle module is set to be in a low-power state.

In this embodiment of the disclosure, determining the idle module may include determining, for each of the functional modules, if the functional module has not received a user operation within a predetermined time interval, the functional module to be an idle module in an idle state. Alternatively, determining the idle module may include determining, according to the preset workflow, the working time of each of the functional modules, and determining the functional module, which is not in the working time, as the idle module in the idle state. Alternatively, determining the idle module may include receiving an instruction that is input by a user for designating an idle module among the functional modules, and determining the idle module among the functional modules according to the instruction.

In this embodiment of the disclosure, the low-power state may include a state in which the power consumption is lower than the power consumption in a working state, with the working state including a power-on state. The low-power state of each of the functional modules includes a sleep state and a power-off state.

In this embodiment of the disclosure, the method 400 may also include (not shown): allowing the main control circuit to be in the low-power state when all the functional modules are set to be in the low-power state. The low-power state of the main control circuit includes a sleep state.

In this embodiment of the disclosure, the method 400 may also include (not shown): waking up the main control circuit itself and/or the idle module on the basis of the user operation.

Based on the above description, on the basis of the control method for a medical device according to this embodiment of the disclosure, an idle module in a idle state is determined in real time, and the idle module is set to be in a low-power state, thereby reducing the overall power consumption of the medical device and improving the battery life of the medical device.

Figure 5:
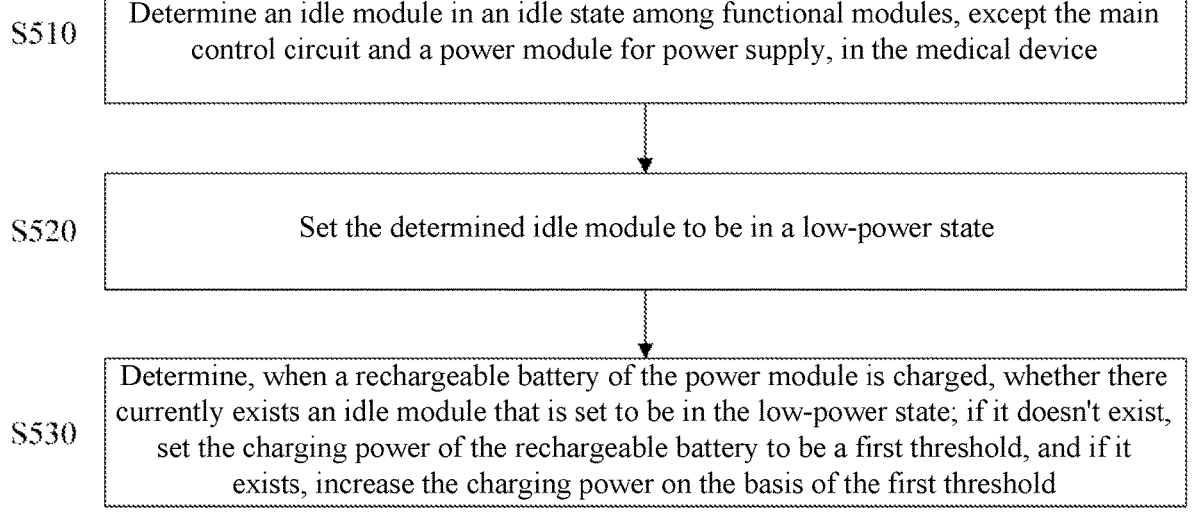
FIG. 5 shows a schematic flow diagram of a control method for a medical device according to another embodiment of the disclosure.

FIG. 5 shows a schematic flow diagram of a control method 500 for a medical device according to another embodiment of the disclosure. As shown in FIG. 5, the control method 500 for the medical device may include the following steps.

At step S510, an idle module in an idle state among functional modules, except the main control circuit and a power module for power supply, in the medical device is determined.

At step S520, the determined idle module is set to be in a low-power state.

At step S530, when the rechargeable battery of the power module is charged, it is determined whether there currently exists an idle module that is set to be in the low-power state, if it doesn't exist, the charging power of the rechargeable battery is set to be a first threshold, and if it exists, the charging power is increased on the basis of the first threshold.

In this embodiment of the disclosure, the charging power of the rechargeable battery may be determined according to the power consumption of the idle module that is set to be in the low-power state. Based on this, the increased charging power on the basis of the first threshold may be equal to the sum of reduced power consumption of each functional module, which is set to be in the low-power state, relative to the power consumption in the working state.

In this embodiment of the disclosure, the method 500 may also include (not shown): selecting a suitable charging level from the preset charging levels according to the number of the idle modules that are set to be in the low-power state, with different charging levels corresponding to different charging powers.

Based on the above description, on the basis of the control method for a medical device according to this embodiment of the disclosure, an idle module in a idle state is determined in real time, and the idle module is set to be in a low-power state, thereby reducing the overall power consumption of the medical device and improving the battery life of the medical device. In addition, on the basis of the control method for a medical device according to this embodiment of the disclosure, the power consumption of each of the functional modules is determined in real time when the rechargeable power module thereof is charged, and the charging power of the rechargeable power module thereof is adjusted when the total power consumption of all the functional modules changes, thereby improving the charging flexibility and providing the possibility to increase the charging speed.

Figure 6:
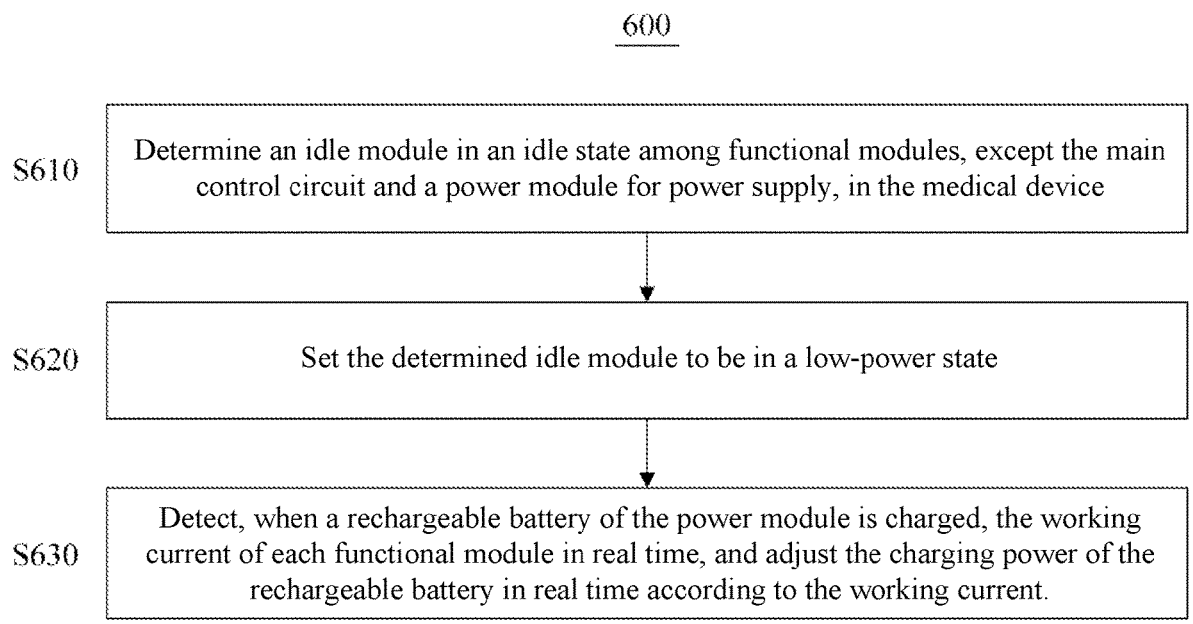
FIG. 6 shows a schematic flow diagram of a control method for a medical device according to still another embodiment of the disclosure.

FIG. 6 shows a schematic flow diagram of a control method for a medical device 600 according to another embodiment of the disclosure. As shown in FIG. 6, the control method 600 for the medical device may include the following steps.

At step S610, an idle module in an idle state among functional modules, except the main control circuit and a power module for power supply, in the medical device is determined.

At step S620, the determined idle module is set to be in a low-power state.

At step S630, when the rechargeable battery of the power module is charged, the working current of each functional module is detected in real time, and the charging power of the rechargeable battery is adjusted in real time according to the working current.

In the embodiments of the disclosure, the main control circuit does not adjust the charging power of the rechargeable battery of the power module on the basis of whether there is an idle module, but monitors the working current of each functional module in real time and adjusts the charging power of the rechargeable battery in real time according to the working current. In this embodiment, regardless of whether the functional module enters the low-power state, the working current of each functional module is monitored in real time, and once the working current of the functional module is detected to be reduced, it indicates that there is a room for increasing the charging power of the rechargeable battery of the power module. In this case, the charging power of the rechargeable battery of the power module may be further correspondingly increased on the basis of the overall reduction in power consumption of all the functional modules, thereby increasing the charging speed. Thereafter, the main control circuit may continue to monitor the working current of each functional module in real time, and once the working current of the functional module is detected to be increased, the charging power of the rechargeable battery of the power module is also correspondingly reduced. According to this embodiment, it is not only possible to increase the charging speed of the rechargeable battery of the power module, and also achieve the very flexible adjustment of the charging power.

Based on the above description, on the basis of the control method for a medical device according to this embodiment of the disclosure, an idle module in a idle state is determined in real time, and the idle module is set to be in a low-power state, thereby reducing the overall power consumption of the medical device and improving the battery life of the medical device. In addition, on the basis of the control method for a medical device according to this embodiment of the disclosure, the power consumption of each of the functional modules is determined in real time when the rechargeable power module thereof is charged, and the charging power of the rechargeable power module thereof is adjusted when the total power consumption of all the functional modules changes, thereby improving the charging flexibility and providing the possibility to increase the charging speed.

Figure 7:
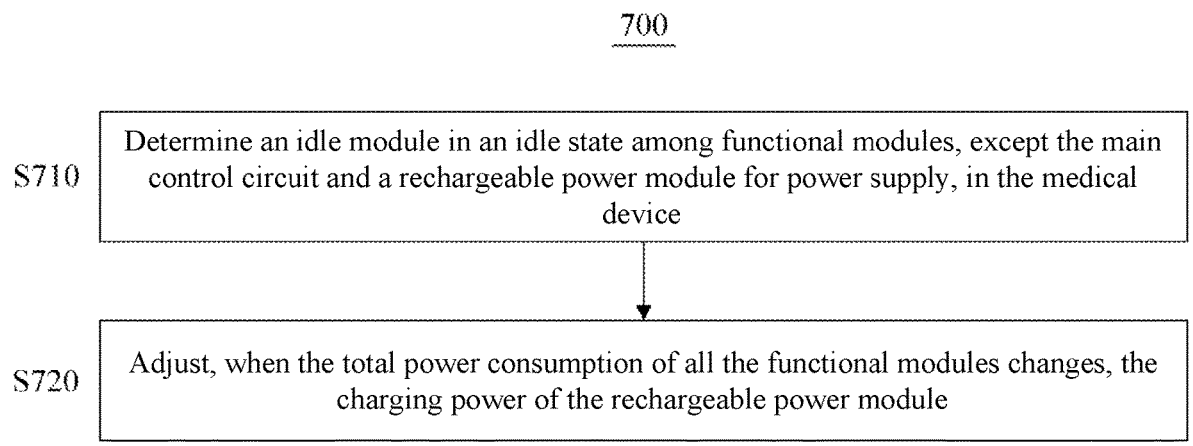
FIG. 7 shows a schematic flow diagram of a control method for a medical device according to yet another embodiment of the disclosure.

FIG. 7 shows a schematic flow diagram of a control method for a medical device 700 according to another embodiment of the disclosure. As shown in FIG. 7, the control method 700 for the medical device may include the following steps.

At step S710, when the rechargeable power module of the medical device is charged, the power consumption of the functional modules, except the main control circuit and the rechargeable power module, in the medical device is determined.

At step S720, when the total power consumption of all the functional modules changes, the charging power of the rechargeable power module is adjusted.

In this embodiment of the disclosure, adjusting the charging power of the rechargeable power module may include: increasing the charging power of the rechargeable power module when the total power consumption of all the functional modules is reduced; and reducing the charging power of the rechargeable power module when the total power consumption of all the functional modules is increased.

In this embodiment of the disclosure, when the power consumption of each of the functional modules reaches the maximum value, the charging power of the rechargeable power module may be equal to the first threshold; and when the power consumption of any one of the functional modules does not reach the maximum value, the charging power of the rechargeable power module may be equal to a second threshold, which may be equal to the first threshold plus the reduced value, relative to the maximum value, of the power consumption value of the power module that does not reach the maximum value.

In this embodiment of the disclosure, determining the power consumption of each of the functional modules includes: detecting the working current of each of the functional modules in real time, and determining the power consumption of each of the functional modules according to the working current of each of the functional modules.

In this embodiment of the disclosure, adjusting the charging power of the rechargeable power module may include: adjusting the charging current of the rechargeable power module.

Based on the above description, on the basis of the control method for a medical device according to this embodiment of the disclosure, the power consumption of each of the functional modules is determined in real time when the rechargeable power module thereof is charged, and the charging power of the rechargeable power module thereof is adjusted when the total power consumption of all the functional modules changes, thereby improving the charging flexibility and providing the possibility to increase the charging speed.

Figure 8:
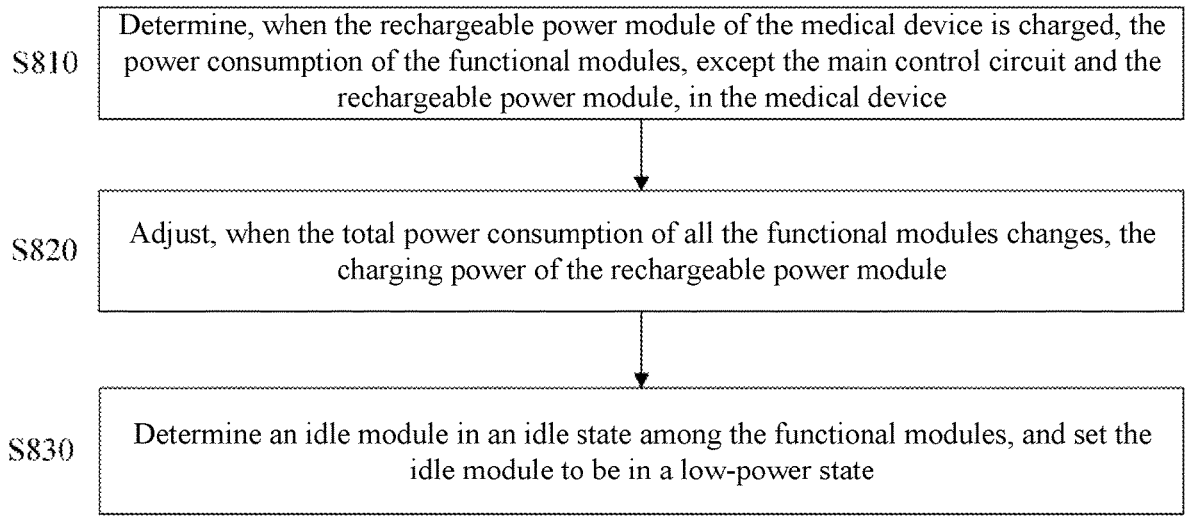
FIG. 8 shows a schematic flow diagram of a control method for a medical device according to still another embodiment of the disclosure.

FIG. 8 shows a schematic flow diagram of a control method for a medical device 800 according to another embodiment of the disclosure. As shown in FIG. 8, the control method 800 for the medical device may include the following steps.

At step S810, when the rechargeable power module of the medical device is charged, the power consumption of the functional modules, except the main control circuit and the rechargeable power module, in the medical device is determined.

At step S820, when the total power consumption of all the functional modules changes, the charging power of the rechargeable power module is adjusted.

At step S830, an idle module in an idle state among the functional modules is determined, and the idle module is set to be in a low-power state.

In this embodiment of the disclosure, determining the idle module may include determining, for each of the functional modules, if the functional module has not received a user operation within a predetermined time interval, the functional module to be an idle module in an idle state. Alternatively, determining the idle module may include determining, according to the preset workflow, the working time of each of the functional modules, and determining the functional module, which is not in the working time, as the idle module in the idle state. Alternatively, determining the idle module may include receiving an instruction that is input by a user for designating an idle module among the functional modules, and determining the idle module among the functional modules according to the instruction.

In this embodiment of the disclosure, the low-power state may include a state in which the power consumption is lower than the power consumption in a working state, with the working state including a power-on state. The low-power state of each of the functional modules includes a sleep state and a power-off state.

In this embodiment of the disclosure, the method 800 may also include (not shown): allowing the main control circuit to be in the low-power state when all the functional modules are set to be in the low-power state. The low-power state of the main control circuit includes a sleep state.

In this embodiment of the disclosure, the method 800 may also include (not shown): waking up the main control circuit itself and/or the idle module on the basis of the user operation.

In this embodiment of the disclosure, the medical device controlled by means of the methods 400 to 800 may be switched between at least two working modes, with at least one preset workflow being included in each of the working modes, the preset workflow including at least one medical function, and the medical functions included in the two working modes being at least partially the same. The user may understand the working mode described here according to the foregoing description in conjunction with FIG. 1, which will not be further described here for brevity.

Based on the above description, on the basis of the control method for a medical device according to this embodiment of the disclosure, the power consumption of each of the functional modules is determined in real time when the rechargeable power module thereof is charged, and the charging power of the rechargeable power module thereof is adjusted when the total power consumption of all the functional modules changes, thereby improving the charging flexibility and providing the possibility to increase the charging speed. In addition, on the basis of the control method for a medical device according to this embodiment of the disclosure, the idle module in the idle state may be determined in real time, and the idle module is set to be in the low-power state, thereby reducing the overall power consumption of the medical device, improving the battery life of the medical device, and increasing the charging speed of the rechargeable power module when the rechargeable power module is charged.

In a still another aspect according to the disclosure, further provided is a storage medium, which is stored with a computer program that executes the corresponding steps in the control methods 400-800 for the medical device of the embodiments of the disclosure when the computer program is run by a computer or a processor. The storage medium may include, for example, a memory card of a smart phone, a storage component of a tablet computer, a hard disk of a personal computer, a read-only memory (ROM), an erasable programmable read-only memory (EPROM), a portable compact disk read-only memory (CD-ROM), a USB memory, or any combination of the above storage media.

Although the exemplary embodiments have been described here with reference to the accompanying drawings, it should be understood that the exemplary embodiments described above are merely exemplary, and are not intended to limit the scope of the disclosure thereto. Those of ordinary skill in the art may make various changes and modifications therein without departing from the scope and spirit of the disclosure. All such changes and modifications are intended to be included in the scope of the disclosure as claimed in the appended claims.

Those of ordinary skill in the art would have appreciated that the units and algorithm steps of the examples described in conjunction with the embodiments disclosed herein may be implemented in electronic hardware or a combination of computer software and electronic hardware. Whether the functions are performed by hardware or software depends on particular applications and design constraint conditions of the technical solutions. Those skilled in the art could use different methods to implement the described functions for each particular application, but such implementation should not be considered to be beyond the scope of the disclosure.

In several embodiments provided in the disclosure, it should be understood that the disclosed apparatuses and methods could be implemented in other ways. For example, the apparatus embodiment described above is merely schematic, for example, the unit division is merely a logic function division, and in actual implementation, there may be other division methods, for example, multiple units or components may be combined or integrated into another apparatus, or some features can be omitted or not implemented.

A large number of specific details are explained in this specification provided herein. However, it could be understood that the embodiments of the disclosure can be practiced without these specific details. In some instances, well-known methods, structures, and technologies are not shown in detail, so as not to obscure the understanding of this description.

Similarly, it should be understood that in order to simplify the disclosure and help to understand one or more of various aspects of the disclosure, in the description of the exemplary embodiments of the disclosure, various features of the disclosure are sometimes together grouped into an individual embodiment, figure or description thereof. However, the method of the disclosure should not be construed as reflecting the following intention: namely, the disclosure set forth requires more features than those explicitly stated in each claim. More precisely, as reflected by the corresponding claims, the inventive point thereof lies in that features that are fewer than all the features of an individual embodiment disclosed may be used to solve the corresponding technical problem. Therefore, the claims in accordance with the particular embodiments are thereby explicitly incorporated into the particular embodiments, wherein each claim itself serves as an individual embodiment of the disclosure.

Those skilled in the art should understand that, in addition to the case where features are mutually exclusive, any combination may be used to combine all the features disclosed in this specification (along with the appended claims, abstract, and drawings) and all the processes or units of any of methods or apparatuses as disclosed. Unless explicitly stated otherwise, each feature disclosed in this specification (along with the appended claims, abstract, and drawings) may be replaced by an alternative feature that provides the same, equivalent, or similar object.

In addition, those skilled in the art should understand that although some of the embodiments described herein include some but not other features included in other embodiments, combinations of features of different embodiments are meant to be within the scope of the disclosure, and form different embodiments. For example, in the claims, any one of the embodiments set forth thereby can be used in any combination.

Various embodiments regarding components in the disclosure may be implemented in hardware, or implemented by software modules running on one or more processors, or implemented in a combination thereof. It should be understood for those skilled in the art that a microprocessor or a digital signal processor (DSP) may be used in practice to implement some or all of the functions of some modules according to this embodiment of the disclosure. The disclosure may further be implemented as an apparatus program (e.g. a computer program and a computer program product) for executing some or all of the methods described herein. Such a program for implementing the disclosure may be stored on a computer-readable medium, or may be in the form of one or more signals. Such a signal may be downloaded from an Internet website, or provided on a carrier signal, or provided in any other form.

It should be noted that the description of the disclosure made in the above-mentioned embodiments is not to limit the disclosure, and those skilled in the art may design alternative embodiments without departing from the scope of the appended claims. In the claims, any reference signs placed between parentheses should not be construed as limitation on the claims. The disclosure may be implemented by means of hardware including several different elements and by means of an appropriately programmed computer. In unit claims listing several apparatuses, several of these apparatuses may be specifically embodied by one and the same item of hardware. The use of the terms "first", "second", "third", etc. does not indicate any order. These terms may be interpreted as names.

The above descriptions are merely the specific embodiments of the disclosure or the description of the specific embodiments, but the scope of protection of the disclosure is not limited thereto. Any changes or substitutions readily conceivable by those skilled in the art within the technical scope disclosed in the disclosure shall fall within the scope of protection of the disclosure. Therefore, the scope of protection of the disclosure should be subject to the scope of protection of the claims.

What is claimed is:

1. A medical device, which is switched between at least two working modes including a continuous monitoring working mode and a discontinuous monitoring working mode, with at least one preset workflow being included in each of the working modes, the preset workflow comprising at least one medical function, and the medical functions included in the two working modes being at least partially the same,
the medical device comprising a main control circuit, a power module, and functional modules for implementing the medical functions of the medical device in both working modes, with the functional modules being powered by the power module and controlled by the main control circuit, wherein the main control circuit is used to determine an idle module in an idle state among the functional modules and set the idle module to be in a low-power state;
wherein one of the functional modules is a parameter measurement circuit configured to implement a parameter measurement function in both working modes.

2. The medical device of claim 1, wherein to determine an idle module, the main control circuit is used to: for each of the functional modules, if the functional module has not received a user operation within a predetermined time interval, determine the functional module to be the idle module in the idle state.

3. The medical device of claim 1, wherein to determine an idle module, the main control circuit is used to: determine, according to the preset workflow, a working time of each of the functional modules; and determine the functional module, which is not in the working time, to be the idle module in the idle state.

4. The medical device of claim 1, wherein when each of the functional modules is set to be in the low-power state, the main control circuit enters into a low-power state.

5. The medical device of claim 1, wherein the low-power state includes a state in which a power consumption is lower than that in a working state which includes a power-on state, and wherein the low-power state of each of the functional modules includes a sleep state and a power-off state, and the low-power state of the main control circuit includes a sleep state.

6. The medical device of claim 1, wherein the power module comprises a rechargeable battery,
wherein when the rechargeable battery is charged, the main control circuit is further used to:
determine whether there currently exists an idle module that is set to be in the low-power state;
if it doesn't exist, set a charging power of the rechargeable battery to be a first threshold; and
if it exists, increase the charging power based on the first threshold.

7. The medical device of claim 6, wherein the main control circuit is further used to determine the charging power of the rechargeable battery according to a power consumption of the idle module that is set to be in the low-power state.

8. The medical device of claim 6, wherein the increased charging power based on the first threshold is equal to a sum of reduced power consumption of each functional module, which is set to be in the low-power state, relative to a power consumption in a working state.

9. The medical device of claim 6, wherein the main control circuit is further used to select a suitable charging level from preset charging levels according to a number of idle modules that are set to be in the low-power state, wherein different charging levels correspond to different charging powers.

10. The medical device of claim 1, wherein the power module comprises a rechargeable battery,
wherein when the rechargeable battery is charged, the main control circuit is further used to detect a working current of each of the functional modules in real time and adjust a charging power of the rechargeable battery according to the working current in real time.

11. The medical device of claim 1, wherein the functional modules further include at least one of a display, an alarm circuit and an interface circuit.

12. A medical device, which is switched between at least two working modes including a continuous monitoring working mode and a discontinuous monitoring working mode, with at least one preset workflow being included in each of the working modes, the preset workflow/comprising at least one medical function, and the medical functions included in the two working modes being at least partially the same,
wherein the medical device comprises a main control circuit, a rechargeable power module, and functional modules for implementing the medical functions of the medical device in both working modes, with the functional modules being powered by the rechargeable power module and controlled by the main control circuit, wherein the main control circuit is used to determine a power consumption of each of the functional modules when the rechargeable power module is charged, and adjust a charging power of the rechargeable power module when a total power consumption of all the functional modules changes.

13. The medical device of claim 12, wherein to adjust the charging power of a rechargeable power module, the main control circuit is further used to: increase the charging power of the rechargeable power module when the total power consumption of all the functional modules is reduced; and reduce the charging power of the rechargeable power module when the total power consumption of all the functional modules is increased,
wherein when the power consumption of each of the functional modules reaches a maximum value, the charging power of the rechargeable power module is equal to a first threshold; and when the power consumption of any one of the functional modules does not reach a maximum value, the charging power of the rechargeable power module is equal to a second threshold, which is equal to the first threshold plus a reduced value, relative to the maximum value, of the power consumption of the functional module that does not reach the maximum value.

14. The medical device of claim 12, wherein to determine the power consumption of each of the functional modules, the main control circuit is further used to: detect a working current of each of the functional modules in real time, and determine the power consumption of each of the functional modules according to the working current of each of the functional modules.

15. The medical device of claim 12, wherein to adjust the charging power of the rechargeable power module, the main control circuit is further used to: adjust a charging current of the rechargeable power module.

16. The medical device of claim 12, wherein the main control circuit is further used to determine an idle module in an idle state among the functional modules and set the idle module in a low-power state.

17. The medical device of claim 16, wherein to determine the idle module, the main control circuit is further used to:
for each of the functional modules, if the functional module has not received a user operation within a predetermined time interval, determine the functional module to be the idle module in the idle state; or,
determine, according to the preset workflow, a working time of each of the functional modules, and determine the functional module, which is not in the working time, to be the idle module in the idle state.

18. The medical device of claim 16, wherein when each of the functional modules is set to be in the low-power state, the main control circuit enters into a low-power state, wherein the low-power state includes a state in which a power consumption is lower than that in a working state which includes a power-on state.

19. The medical device of claim 18, wherein the low-power state of each of the functional modules includes a sleep state and a power-off state, and the low-power state of the main control circuit includes a sleep state.

20. The medical device of claim 12, wherein the functional modules include at least one of a parameter measurement circuit, a display, an alarm circuit and an interface circuit.

* * * * *